United States Patent
Zeiss

[11] Patent Number: 4,777,279
[45] Date of Patent: Oct. 11, 1988

[54] PROCESS FOR THE PREPARATION OF L-HOMOALANIN-4-YL(METHYL)-PHOSPHINIC ACID AND ITS ALKYL ESTERS

[75] Inventor: Hans-Joachim Zeiss, Sulzbach, Fed. Rep. of Germany

[73] Assignee: Hoechst Aktiengesellschaft, Frankfurt am Main, Fed. Rep. of Germany

[21] Appl. No.: 936,335

[22] Filed: Dec. 1, 1986

[30] Foreign Application Priority Data

Dec. 3, 1985 [DE] Fed. Rep. of Germany ....... 3542645

[51] Int. Cl.$^4$ ............................................. C07F 9/32
[52] U.S. Cl. ....................................... 558/145; 558/174
[58] Field of Search ......................................... 558/145

[56] References Cited

U.S. PATENT DOCUMENTS 4,599,207  7/1986  Lachheim et al. ................... 558/137

FOREIGN PATENT DOCUMENTS 0127429 12/1984 European Pat. Off. .

*Primary Examiner*—Anton H. Sutto
*Attorney, Agent, or Firm*—Curtis, Morris & Safford

[57] ABSTRACT

Process for the preparation of L-homoalanin-4-yl(methyl)-phosphinic acid (esters) of the formula I

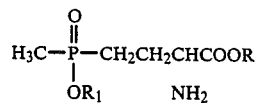

(R, $R_1$=H, alkyl) or salts thereof by reacting an R-3-isopropyl-2,5-dialkoxy-3,6-dihydropyrazine of the formula II with a β-halogenoethyl(methyl)phosphinic acid ester of the formula IV

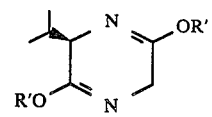

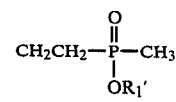

(R', $R_1'$=alkyl) to give compounds of the formula V

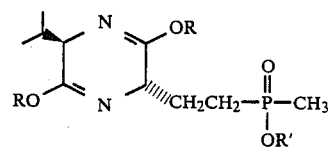

and then subjecting the latter to hydrolytic cleavage.

3 Claims, No Drawings

PROCESS FOR THE PREPARATION OF L-HOMOALANIN-4-YL(METHYL)-PHOSPHINIC ACID AND ITS ALKYL ESTERS

The present invention relates to a process for the preparation of L-homoalanin-4-yl(methyl)-phosphinic acid (esters) of the general formula I

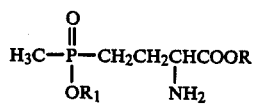  I in which R and R₁ are identical or different and denote hydrogen or $(C_1-C_6)$-alkyl, and of salts thereof with inorganic or organic acids or bases.

L-homoalanin-4-yl(methyl)phosphinic acid, described below as L-phosphinothricin or L-Ptc for short, its esters and its salts with organic or inorganic acids or bases are, as described in German Offenlegungsschrift No. 2,856,260, the active enantiomers of the herbicidally effective racemates described in German Offenlegungsschrift No. 2,717,440. According to German Offenlegungsschrift No. 2,856,260, the herbicidal action of L-Ptc against numerous monocotyledonous and dicotyledonous annual and perennial weeds is twice as great as that of the racemates. By using pure L-Ptc instead of the racemate it is therefore possible to reduce the application rate of the herbicide by one half, as a result of which possible undersirable side effects are also correspondingly reduced.

Hitherto, however, the difficulties in the preparation of L-Ptc have stooed in the way of its wide use.

Although the acid or enzymatic cleavage of the antibiotic SF-1293 containing L-Ptc is described in Japanese Published Specification Nos. 73-85,538 and 74-31,890, the preparation of the latter by a fermentation route, such as is described, for example, in German Offenlegungsschrift No. 2,236,599, is very involved.

The cleavage of N-acylated D,L-Ptc derivatives by means of acylases is also known, either (a) by means of microbial acylase in accordance with German Offenlegungsschrift No. 2,939,269 or (b) by using penicillin-G-acylase in accordance with German Offenlegungsschrift No. 3,048,612. Disadvantages are, in process (a) the low optical purity of the resulting L-Ptc, and in (b), the involved working up of the crude products via ion exchangers and the relatively high costs of the phenylacetic acid required for the acylation.

The only non-enzymatic process hitherto dissolved for the preparation of L-Ptc, which is described in European Published Specification No. 127,429, uses a chiral, non-racemic imine as the starting material in order to synthesize the chiral carbon atom in L-Ptc in an alkylation reaction, following the principle of asymmetric induction (for an explanation of the term see: E. L. Eliel: Stereochemie der Kohlenstoffverbindungen ("The stereochemistry of carbon compounds") pasges 23-30, Verlag Chemie, Weinheim 1966).

It is a disadvantage in this process, however, that the expensive chiral auxiliary used for the preparation of the chiral imine is required in equimolar amounts and cannot be recovered after the reaction.

It was therefore required to develop a simple process permitting the preparationn of L-phosphinothricin in fairly large amounts and in high optical purity.

The invention therefore relates to a process for the preparation of L-homoalanin-4-yl(methyl)phosphinic acid (esters) of the general formula I and salts thereof, which comprises first converting R-3-isopropyl-2,5-dialkoxy-3,6-dihydropyrazines of the general formula II

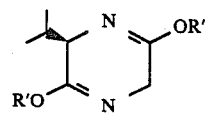  II in which

R' denotes $(C_1-C_4)$-alkyl into the anions III

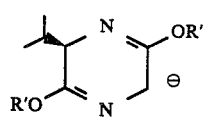  III reacting with a compound of the formula IV

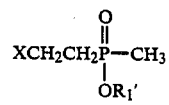  IV in which

R₁' denotes $(C_1-C_6)$-alkyl and

X denotes chlorine, bromine, iodine or a detachable group such as tosylate or mesylate, and subjecting the resulting compounds of the formula V

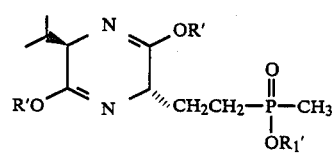  V to hydrolytic cleavage.

The starting materials of the formula II can be prepared in a simple manner from D-valine and glycine analogously to Angew. Chem. 93, 793 (1981). The reaction stage II→III is also known from the literature reference mentioned, although it is described there using as an example the S-enantiomers of II

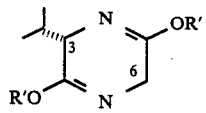

The following may be added here to improve understanding of the symbols L and D or S and R:

D or L establishes the configuration of the carbon atom in the alpha-position relative to the carboxyl group in compounds of the formula I. The designation R is equivalent to the designation D in accordance with generally applicable rules (Angew. Chem. 78, 413 (1966)). Similarly, the designation S is used instead of the designation L. R and S are used to establish the absolute configuration of the particular carbon atom in accordance with the Cahn-Ingold-Prelog nomenclature (Angew. Chem. 78, 413 (1966)).

It is also known from the literature reference that the S-enantiomers of III can be alkylated in position 6 by means of alkyl halides, in the course of which a new center of asymmetry is created in accordance with the principle of asymmetric induction at C-6; this center of asymmetry has the opposite absolute configuration to that of the chirality center at C-3.

It is surprising, however, that substituted alkyl compounds of the formula IV containing a phosphinyl group can also be used as the alkylating agent. This is surprising because normally dialkylphosphinic acid esters of the type IV are converted into tertiary phosphane oxides by organometallic compounds, such as are represented by the anions III (Houben-Weyl; Meth. der org. Chemie ("Methods of organic chemistry"), volume E2, page 34 (1982)).

A detailed description of the individual reaction stages follows:

(a) The anions III are formed by using strong organometallic bases, such as n-butyllithium, lithium diisopropylamide, lithium tetramethylpiperidide or sodium bis(trimethyl silyl)-amide, in an at least equimolar amount, but preferably a 1-1.2-molar amount, relative to II. The solvents used are inert solvents, such as hexane, cyclic ethers, for example tetrahydrofuran or dioxane, or dialkyl ethers, for example diethyl ether, diisopropyl ether or glycol dimethyl ether, but preferably tetrahydrofuran. If necessary, it is also possible to add hexamethylphosphoric acid triamide or 1,3-dimethylimidazolidin-2-one in order to increase the solubility. The reaction temperature is $-80°$ to $-30°$ C., but preferably $-80°$ to $-60°$ C.

(b) The same temperatures and solvents as for (a) are used for the reaction of III with IV. It is advisable to employ the component IV in excess, preferably 1.5 moles per mole of III. The reaction times are between 6 and 24 hours.

(c) The hydrolytic cleavage of compound V is expediently effected by means of an approximately twice molar amount of dilute hydrochloric acid. This produces a mixture of D-valine ester and the compound I in the form of its esters (R' or $R_1'$=alkyl). If desired, these esters can be converted by acid or basic hydrolysis into their salts and the latter can in turn be converted into free L-phosphinothricin. These methods are described, for example, in German Offenlegungsschrift No. 3,048,612.

The separation of the D-valine ester, which only plays the part of a chiral auxiliary in the process according to the invention and which can be re-employed for the synthesis of the starting material II, from the reaction product is effected by known processes, for example by distillation or by extracting the reaction solution, which is weakly alkaline with ammonia, with an organic solvent.

L-phosphinothricin is obtained by the process according to the invention in an optical purity of at least 90%.

The following examples are intended to illustrate the process in greater detail without thereby intending a limitation.

EXAMPLE 1

(3R,6S)-3-isopropyl-6-(2-(3-methylpropoxymethylphosphoryl)ethyl)-2,5-dimethoxy-3,6-dihydropyrazine 5.53 g (0.03 mol) of (3R)-(—)-3-isopropyl-2,5-dimethoxy-3,6-dihydropyrazine ($[\alpha]_D^{25}=-107.5°$, c=1 in ethanol) are dissolved in 50 ml of absolute tetrahydrofuran, and 20.6 ml of a 1.6-molar solution of n-butyllithium in n-hexane are added at $-75°$ C. The reaction mixture is stirred at $-75°$ C. for 15 minutes. A solution, previously cooled to $-60°$ C., of 6.1 g (0.031 mol) of 2-methylpropyl 2-chloroethyl(methyl)phosphinate in 30 ml of tetrahydrofuran is added dropwise in the course of 7 minutes at $-75°$ C. The reaction mixture is stirred for 6 hours at $-75°$ C. and then for 14 hours at room temperature. The solvent is removed completely in vacuo and the residue is taken up in 60 ml of diethyl ether. This solution is extracted once with 60 ml of water and once with 30 ml of saturated sodium chloride solution. The organic phase is dried over MgSO$_4$ and completely freed from solvents. The residue is distilled in a high vacuum. This gives 8.84 g (85.1% of theory) of (3R,6S)-3-isopropyl-6-[2-(3-methylpropoxymethylphosphoryl)ethyl]-2,5-dimethoxy-3,6-dihydropyrazine as a low-melting solid of boiling point 155°–162° C./0.001 bar.

EXAMPLE 2

Isobutyl[L-(3-amino-3-methoxycarbonyl)-prop-1-yl]-(methyl)phosphinate 3.46 g (0.01 mol) of (3R,6S)-3-isopropyl-6-[2-(3-methylpropoxymethylphosphoryl)ethyl]-2,5-dimethoxy-3,6-dihydropyrazine are suspended in 80 ml of 0.25N hydrochloric acid (=0.02 mol) and stirred for 18 hours at room temperature. The pH of the neutral solution is adjusted to 9.5 with ammonia, and the solution is extracted three times with diethyl ether. The combined organic extracts are dried over MgSO$_4$ and concentrated. 1.3 g (=100% of theory) of D-valine methyl ester are left as residue. The aqueous phase is completely freed from solvents, and the residue is taken up in chloroform. The precipitate which has been deposited (ammonium chloride) is filtered off and the filtrate is completely freed from solvents. This gives 2.4 g (95.5% of theory) of isobutyl[L-(3-amino-3-methoxycarbonyl)-prop-1-yl]-(methyl)phosphinate as a colorless oil.

$^1$H-NMR (d$_6$-DMSO): 0.88 (d, J=7.0 Hz, 6H), 1.40 (d, J=14, 0Hz, 3H), 1.57–2,20 (m, 5H), 3.64 (t, J=7, 0Hz, 2H), 3.72 (s, 3H), 3.83–4,02 (m, broad, 1H) $[\alpha]_D^{22}=13.8°$ (c=3.24 in 1N HCl).

EXAMPLE 3

L-Homoalanin-4-yl(methyl)phosphinic acid (a) 2.0 g (0.008 mol) of isobutyl[L-(3-amino-3-methoxycarbonyl)-prop-1-yl]-(methyl)phosphinate are dissolved in 50 ml of 6N hydrochloric acid, and the mixture is boiled under reflux for 15.5 hours. The aqueous solution is completely freed from solvents, and the residue which remains is freed from water azeotropically using acetone/toluene. 1.5 g (86.7% of theory) of L-homoalanin-4-yl(methyl)phosphinic acid hydrochloride are obtained as a white solid, which is purified by recrystallization from an ethanol/water mixture.

Melting point 197°–199° C. (decomposition), $[\alpha]_D^{22}=22.5°$ (c=1.96 in 1N HCl)

(b) 0.291 g of the hydrochloride is dissolved in ethanol/water, and 0.1 g of propene oxide is added. After the mixture has stood for one day at room temperature, 0.17 g (72.2% of theory) of L-homoalanin-4-yl(methyl)phosphinic acid is obtained as a white solid of melting point 214°–16° C. (decomposition), with an angle of rotation $[\alpha]_D^{22}$ of 15.9° (c=1.04 in H$_2$O). This corresponds to an optical purity of at least 93%, relative to $[\alpha]_D^{23}=17°$ (c=1 in H$_2$O) for optically pure L-homoalanin-4-yl (methyl)phosphinic acid [Sci. Reports of Meiji Seika Kaisha 13, 42 (1973)].

I claim:

1. A process for the preparation of L-homoalanin-4-yl(methyl)phosphinic acid (esters) of the formula

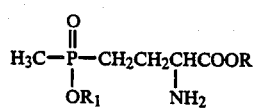   I in which

R and R$_1$ are identical or different and are hydrogen or (C$_1$–C$_6$)-alkyl, and of salts thereof, which comprises first converting R-3-isopropyl-2,5-dialkoxy-3,6-dihydropyrazines of the formula II

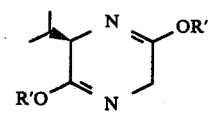   II in which

R' is (C$_1$–C$_4$)-alkyl, using strong organometallic bases at a temperature of from about −80° to −30° C., into the anions III

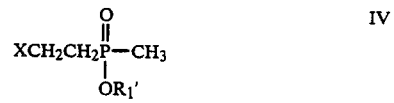   III reacting these anions with a compound of the formula IV $$XCH_2CH_2\overset{\overset{O}{\|}}{\underset{\underset{OR_1'}{|}}{P}}-CH_3 \quad IV$$

in which

R$_1'$ is (C$_1$–C$_6$)-alkyl and

X is chlorine, bromine, iodine or a detachable group such as tosylate or mesylate, at a temperature of from about −80° to −30° C., and subjecting the resulting compounds of the formula V

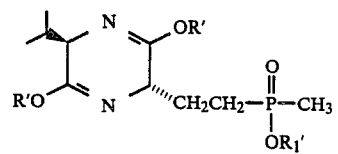   V to hydrolytic cleavage.

2. The process as claimed in claim 1, wherein the strong organometallic base used for the conversion into the anion III is selected from the group consisting of N-butyllithium, lithium diisopropylamide, lithium tetramethylpiperidide or sodium bis(trimethylsilyl)-amide.

3. The process as claimed in claim 1, wherein the reaction is carried out at −60° C. to −80° C.

* * * * *